United States Patent
Mikhnenko et al.

(10) Patent No.: US 12,385,890 B2
(45) Date of Patent: Aug. 12, 2025

(54) SYSTEM AND METHOD FOR MEASURING INDIVIDUAL AIR POLLUTANT EXPOSURE

(71) Applicants: Igor Mikhnenko, Kharkov (UA); Vera Kozyr, St. Petersburg (RU); Alexey Pyshkin, St. Petersburg (RU); Dmitry Lukashev, St. Petersburg (RU); Alexander Masalov, St. Petersburg (RU)

(72) Inventors: Igor Mikhnenko, Kharkov (UA); Vera Kozyr, St. Petersburg (RU); Alexey Pyshkin, St. Petersburg (RU); Dmitry Lukashev, St. Petersburg (RU); Alexander Masalov, St. Petersburg (RU)

(73) Assignee: Atmotech, Inc., San Francisco, CA (US)

( * ) Notice: Subject to any disclaimer, the term of this patent is extended or adjusted under 35 U.S.C. 154(b) by 473 days.

(21) Appl. No.: 17/825,772

(22) Filed: May 26, 2022

(65) Prior Publication Data
US 2022/0381466 A1  Dec. 1, 2022

Related U.S. Application Data

(60) Provisional application No. 63/193,861, filed on May 27, 2021.

(51) Int. Cl.
*G01N 33/00* (2006.01)
*F24F 11/49* (2018.01)
*F24F 110/50* (2018.01)
*F24F 120/10* (2018.01)
*F24F 120/12* (2018.01)

(52) U.S. Cl.
CPC .......... *G01N 33/0032* (2013.01); *F24F 11/49* (2018.01); *G01N 33/0037* (2013.01); *G01N 33/004* (2013.01); *G01N 33/0068* (2024.05); *G01N 33/0075* (2013.01); *F24F 2110/50* (2018.01); *F24F 2120/10* (2018.01); *F24F 2120/12* (2018.01); *G01N 33/0006* (2013.01); *G01N 33/0031* (2013.01); *G01N 33/0062* (2013.01); *G01N 33/0073* (2013.01)

(58) Field of Classification Search
CPC .......... G01N 33/0032; G01N 33/0037; G01N 33/004; G01N 33/0068; G01N 33/0075; G01N 33/0031; G01N 33/0062; G01N 33/0073; F24F 11/49; F24F 2110/50; F24F 2120/10; F24F 2120/12
See application file for complete search history.

(56) References Cited

U.S. PATENT DOCUMENTS

| 10,139,384 B1 * | 11/2018 | Nourbakhsh | G01N 33/0075 |
| 2019/0004023 A1 * | 1/2019 | Kelly | G01D 3/08 |
| 2020/0143561 A1 * | 5/2020 | Hallett | G06T 7/13 |

FOREIGN PATENT DOCUMENTS

CN  110672148 A  *  1/2020  ............. G01D 21/02

* cited by examiner

*Primary Examiner* — Benjamin R Schmitt
(74) *Attorney, Agent, or Firm* — Larisa Migachyov

(57) ABSTRACT

An air quality monitor connected to a server that can identify individual people as they move from room to room count the people in each room; the information is then used to determine each person's individual exposure to pollutants.

7 Claims, 6 Drawing Sheets

SYSTEM AND METHOD FOR MEASURING INDIVIDUAL AIR POLLUTANT EXPOSURE

CROSS-REFERENCE TO RELATED APPLICATIONS

The present application takes priority from Provisional Application No. 63/193,861, filed May 27, 2021, which is incorporated herein by reference.

BACKGROUND

Field of the Invention

The present invention pertains to air quality monitoring systems, and in particular to an indoor air quality monitoring system that can track an individual person's cumulative pollutant exposure.

Background of the Invention

Poor indoor air quality is a serious problem, and especially serious in office buildings and other buildings where occupants spend the majority of their working time. Employee exposure to various pollutants can lead to health problems and legal issues for the employer.

For example, cumulative exposure to particulate matter such as PM2.5 may be correlated with various health problems such as heart attacks, asthma, decreased lung function, various respiratory symptoms, and premature death in people with heart or lung disease. Exposure to Volatile Organic Compounds (VOC's) can cause damage to liver, kidneys, and central nervous system.

Various systems exist for tracking an individual's pollutant exposure as they move around a building. Some of those systems track individuals by means of wearable devices or mobile phones. However, a system that depends only on wearable devices is an expensive and complex one, requiring multiple expensive electronic devices for every building visitor. Furthermore, a system that depends solely on wearable devices is not going to be able to track pollutant exposure for occupants who do not have them, whose devices are turned off. At the same time, a system that does not use mobile phone data when it is available is a system that is more complex than it needs to be; if an individual can be identified from a mobile phone, there is no need to engage in further analysis.

A need exists for a system and method for measuring individual pollutant exposure that does not rely on wearables or mobile phones alone.

SUMMARY OF THE INVENTION

An object of the present invention is to provide a system and method for measuring indoor air quality.

Another object of the present invention is to provide a system and method for tracking an individual's exposure to indoor pollutants.

The system of the present invention comprises a plurality of air quality monitors located in different locations within the building. Each air quality monitor comprises at least one sensor for detecting at least one air pollutant, a RF scanner for detecting RF signals such as the signals emitted by a mobile phone, a radar scanner to detect living humans, a communication module for communicating with a server, and a processor and memory. The air quality monitors are connected to a server. The server receives air quality data from each air quality monitor. Each air quality monitor also uses its radar scanner to detect any living humans present in the vicinity of the air quality monitor and its RF scanner to detect any mobile devices present in the vicinity of the air quality monitor. The air quality monitor then identifies each mobile device present and correlates the mobile device data to the radar data to determine which living humans are carrying which mobile devices. For each living human, the mobile device data and the radar data are combined into a unique personal signature that is then uploaded to the server, with a timestamp. If no mobile device data is present, the unique personal signature consists of radar data alone. If no radar data is present, the unique personal signature consists of mobile data alone.

Once a unique personal signature is generated and uploaded to the server, the server compares it to other unique personal signatures stored on the server. If it matches a stored unique personal signature, the server identifies the person and records the time and location of the person. If it does not match a stored unique personal signature, the server stores the new unique personal signature and therefore creates an identifier for the person, for future tracking, and records the time and location of the person.

In a situation where two or more air quality monitors are located in the same room, the two air quality monitors may record the same person's unique personal signature. In an embodiment, the server identifies a duplicate unique personal signature from two or more air quality monitors in the same room and either combines the two unique personal signatures into one or deletes one of them.

The radar data used to form part or all of the unique personal signature can be related to size, shape, or movement patterns. In an embodiment, some of the information in the radar data is eliminated as irrelevant.

The RF and radar scans are preferably performed at regular intervals to ensure that each person's entrance and exit time are recorded accurately. Those intervals can be 10 seconds, 30 seconds, 1 minute, 2 minutes, 5 minutes, 10 minutes, 15 minutes, or any other time interval. Alternately, the scans can be triggered by motion within the vicinity of an air quality monitor.

Once the person's entrance and exit time for each air quality monitor are recorded, the data is then combined with the air quality data recorded by each air quality monitor and used by the server to determine the person's cumulative pollution exposure.

Unique personal signatures are anonymized and there is no direct identifier such as a name or any other identifier which allows the exact person to be identified directly. Unique personal signatures should be stored for the duration of the person's cumulative pollution exposure. The duration can be a work shift (8 hours), 24 hours, 1 week, 2 weeks, 1 month, 1 quarter, 1 year, or any other duration.

LIST OF FIGURES

DETAILED DESCRIPTION

The system and method of the present invention allows determining both a precise concentration of air pollutants and a precise individual exposure time. Using occupancy detection features of multiple devices, we can track individual exposure in the different locations across the building, as well as the amount of time an individual is spending at a certain location. Results can be extrapolated to more accurate potential dose/applied dose/internal dose and biologically effective dose formulas, which would benefit employee health management.

This information can be used to optimize HVAC system operation to keep air quality and indoor environment within healthy parameters for building occupants, while optimizing energy consumption and reducing HVAC background noise.

The system of the present invention, in an embodiment, comprises a plurality of air quality monitors in various locations in a building. The various locations could be different rooms, or there could be multiple air quality monitors in the same room or space. Any number of air quality monitors may be installed in the building, depending on area and sensor sensitivity. In the preferred embodiment, one air quality monitor is installed in each room, or one per each 30-60 square meters.

Figure 1:
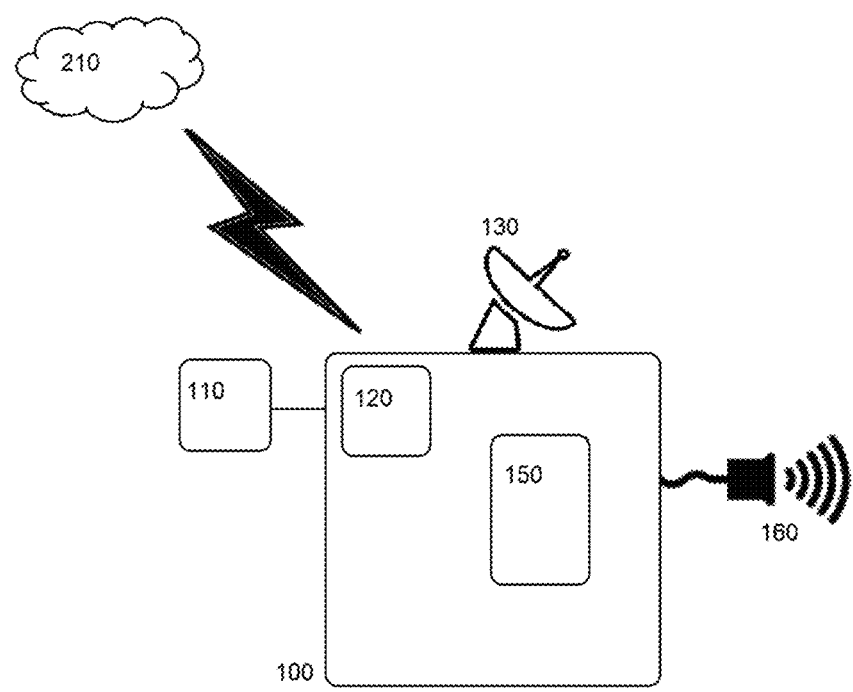
FIG. 1 shows a high-level diagram of one air quality monitor of the present invention.

A sample air quality monitor 100 is shown in FIG. 1. In an embodiment of the present invention, each air quality monitor measures air quality by detecting a range of various pollutants in the air, as well as measuring air temperature, atmospheric pressure, relative humidity, background noise, and ambient light levels. The pollutants that are measured may be any pollutants that may be present in the air and detectable by sensors. In an embodiment of the present invention, the pollutants are VOC, PM, $CO_2$, $CH_2O$ (formaldehyde), ozone, and carbon monoxide, NOx. It will be understood that any other pollutants may also be included. In an embodiment, some of the sensors 110 may be external to the air quality monitor and some sensors 120 may be internal; in an embodiment, the internal sensors measure $CO_2$, PM, VOC, NOx, formaldehyde, ozone and carbon monoxide. In an embodiment, all of the sensors may be external; in another embodiment, all of the sensors may be internal to the air quality monitor. In an embodiment, any external sensors may be connected to the air quality monitor by Bluetooth; in another embodiment, any other wired or wireless connection may be used.

In an embodiment, the air quality monitor may also measure other environmental variables, such as air temperature, atmospheric pressure, relative humidity, background noise, and ambient light levels. It is to be understood that any or all of these variables may be measured by the air quality monitor, and that the list given in this paragraph is not limiting. In an embodiment, air temperature, atmospheric pressure, relative humidity, background noise, and ambient light level sensors may be external or internal.

FIG. 1 shows a high level diagram of the air quality monitor of the present invention. As shown, the air quality monitor 100 comprises internal sensors 120, external sensors 110, and a processor and memory 150.

The air quality monitor also comprises a radar sensor 160. The radar sensor is preferably one that can be used for occupancy sensing. The air quality monitor uses the radar sensor to detect the presence of any people in the area (i.e. in the room or in the near vicinity of the air quality monitor), to determine the approximate position of each person, and to capture radar parameters such as size, shape, and movement patterns. The radar can also count people in its field of view. The radar may be either internal or external. The radar pattern for each person in the area is then stored in the air quality monitor.

The air quality monitor also comprises a Bluetooth or WiFi scanner 130 that can detect RF signals from mobile phones. This is used for identifying any mobile phones present in the area and the approximate distance to each mobile phone or other wearable mobile device. Each mobile device or a combination of mobile devices can then be used to identify a person.

Figure 2:
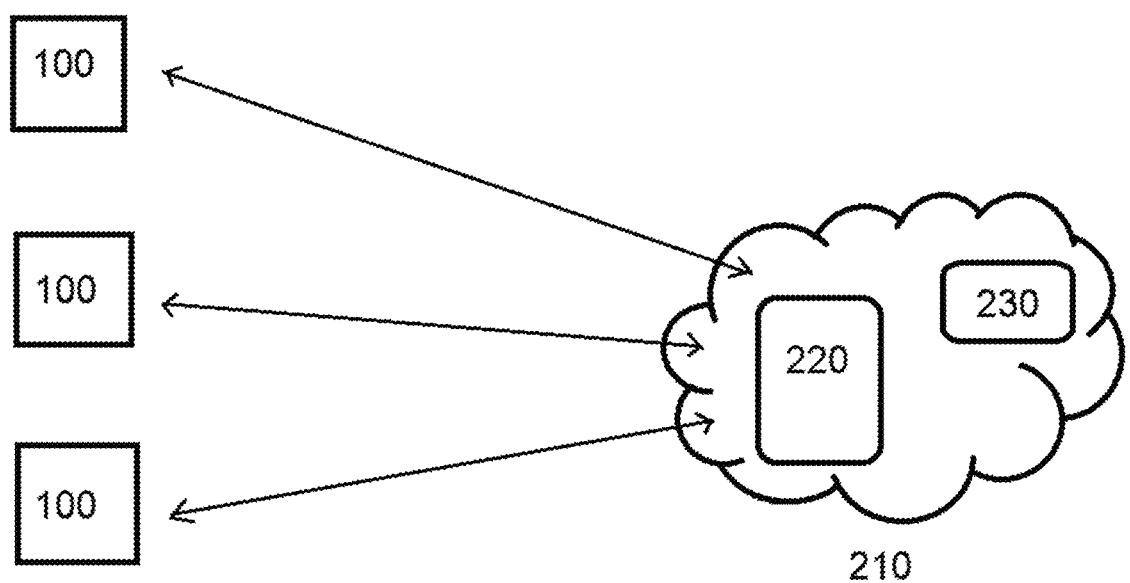
FIG. 2 shows a high-level diagram of the system of the present invention.

The air quality monitor also comprises a connection to a cloud server 210. The air quality monitors are preferably connected to the server by WiFi, Ethernet, Lora, LTE, MQTT, BAC net, Modbus, or other. FIG. 2 shows a diagram of a plurality of air quality monitors 100 connected to the server 210. The server comprises a processing unit 220 and data storage 230 as shown.

In an embodiment, the server comprises information about building floor plans and the location of each air quality monitor, and receives and stores all the data received from each air quality monitor. The server can be located in the same building as the air quality monitors or elsewhere.

One of the objects of the present invention is to track how long an individual spent in each area in the building, and to use that information, along with air quality data from the air quality monitors in each area, to determine the individual's cumulative pollutant exposure. This is useful for employee health and safety and for control of the building's HVAC system.

A method of the present invention comprises identifying an individual in two different ways—from a RF scan that identifies the MAC address of a mobile device, and from a radar scan that identifies the size, shape, and movement patterns of a person. Since each one of these methods may fail for some people (i.e. the RF scan will miss people who aren't carrying their mobile device, while the radar scan may be too vague to identify a person reliably or the person can be away from the radar field of view), combining these two methods is helpful for improving the accuracy of identification and tracking.

In the preferred embodiment of the present invention, each air quality monitor performs regular scans with the radar scanner and the RF scanner. Those two scans may be done simultaneously, or one may be done after the other. In an embodiment, the radar scan is done first. When the air quality monitor performs the radar scan, it detects any living humans in the near vicinity and measures the object signal features from the radar signal—i.e. the object size, shape, location, and movement characteristics. If any living humans are found, it performs a RF scan to identify and record any characteristics of the mobile devices that are broadcasting RF signals. The characteristics may include the MAC address of the mobile device and signal strength, which is then used to calculate the distance between the mobile device and the air quality monitor.

After both scans are performed, the air quality monitor's processor and memory analyze the data and combine the radar data with the mobile device data. Alternately, the air quality monitor can send data to the server, and the server conducts this procedure and sends the results back to the air quality monitor. For example, if a mobile device is identified as being 2 meters from the air quality monitor, and a radar-detected person is identified as being 2 meters from the air quality monitor, the air quality monitor combines the two signals and concludes that the mobile device is being carried by the person. The mobile device information and the radar pattern are then combined into a unique personal signature, which is then transmitted, along with a timestamp, to the server. In cases where no mobile device information is present, the unique personal signature is formed using just the radar pattern. In an embodiment, during this process, any irrelevant data is removed (such as irrelevant wife networks, any radar signals not related to the person, and so on). In cases where radar information is present, the unique personal signature is formed using just mobile device information.

Once the unique personal signature is transmitted to the server, the server runs a check to see if there are any matches for it in a set of unique personal signatures stored on the server. If a match is found, the person is identified and a record of that person's location at the time in the timestamp is created. If no match is found, an identifier is assigned to the unique personal signature, the unique personal signature is stored, and a record of that person's location at the time in the timestamp is created. In an embodiment, all the data stored on the server is deidentified so that the person's name or other personal identifier beside the unique personal signature is not stored or associated with the information. The unique personal signature should be stored for the duration of the person's cumulative pollution exposure, such as 8 hours, 24 hours, 1 week, 2 weeks, 1 month, 1 quarter or a year, or any other duration that can provide useful information.

It must be noted that if there are several air quality monitors in a room, they may create several records for the same person. The server will therefore receive several reports of the same unique personal signature, or similar unique personal signatures. These can be counted as one person if it is known that the air quality monitors creating these reports are located in the same room or in the near vicinity of each other. In an embodiment, the server performs a duplicate check for any unique personal signatures received from nearby air quality monitors and eliminates the duplicate or combines the two duplicate unique personal signatures into one.

The server then uses the received data to create a log for each person's route through the building, including, but not limited to, time spent in any of the rooms or in the vicinity of any of the air quality monitors. The information about the actual number of people in the building can be used to improve the speed and accuracy of this procedure. The data about the actual number of people in the building can be added manually by human input or via external people counters set up on entrances and exits of the building.

The server then uses the log for each person to track each person's individual pollutant exposure for a predetermined time period, by combining the timestamps of presence in each room with the air quality data for that room recorded with the same timestamp by the air quality monitor present in that room. As a result, personal pollution exposure is calculated for a predetermined time period for each person. The system can also determine what room impacted this personal pollution index the most. This information can be communicated to the person, communicated to the person's manager, or used to as an input to the control algorithm of the HVAC system.

In the system with only one air quality monitor or if the air quality monitors are not connected to the cloud, the calculation of person's individual pollutant exposure per each unique personal signature can be done locally by each air quality monitor.

Figure 3A:
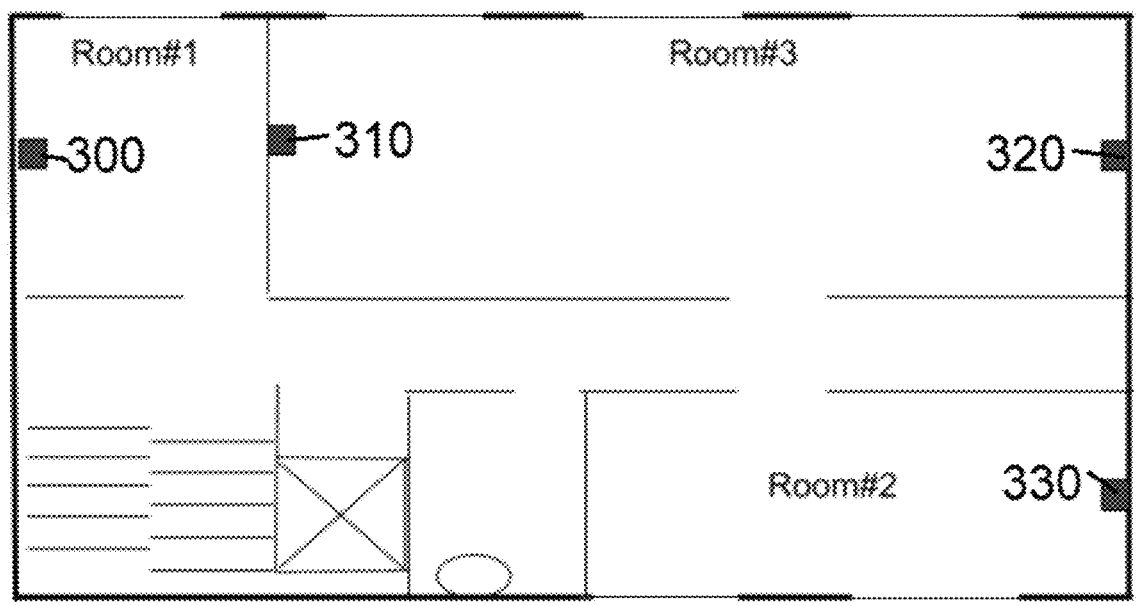
FIG. 3A shows a sample room diagram to illustrate the operation of the system of the present invention.

FIGS. 3A-3D show an example of the tracking algorithm in use. FIG. 3A shows a sample floor plan for the purpose of explaining the algorithm. In the illustrated embodiment, there are three rooms (Room #1, Room #2, and Room #3) and 4 air quality monitors installed, labeled 300, 310, 320, and 330. Each air quality monitor performs regular scans with its radar scanner and RF scanner. These regular scans may be performed in 10 second intervals, 30 second intervals, 1 minute intervals, 2 minute intervals, 5 minute intervals, 10 minute intervals or 15 minute intervals, depending on available resources and desired accuracy. The scans may also be performed based on motion detection, each time a person enters or leaves the room.

Figure 3B:
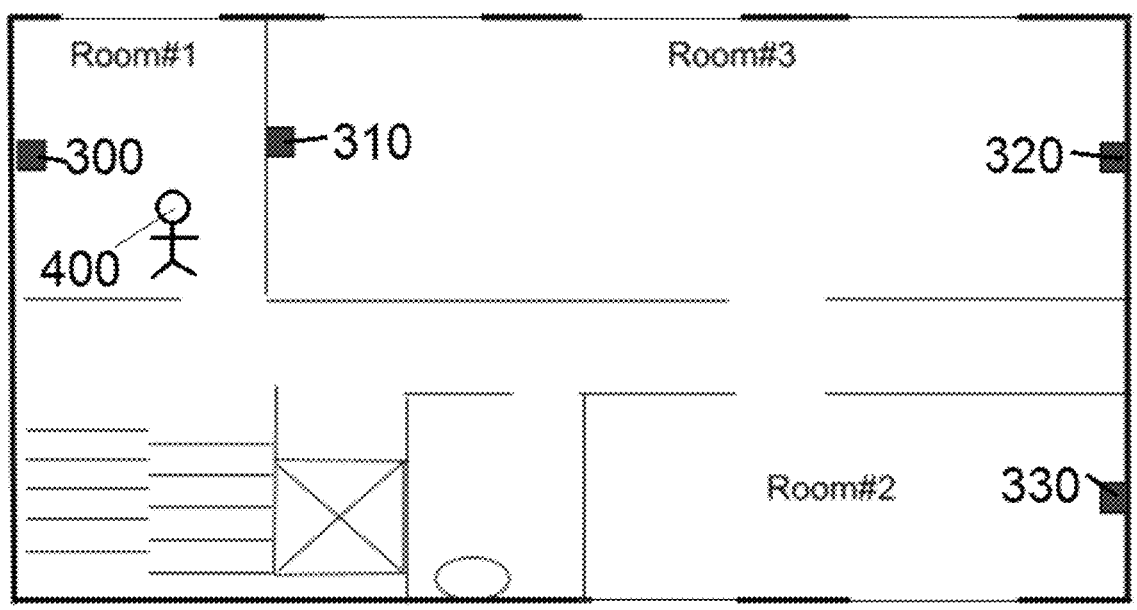
FIG. 3B shows a sample room diagram to illustrate the operation of the system of the present invention.

FIG. 3B shows the same floor plan with a person 400 entering Room #1. The first air quality monitor 300 detects a new person via radar and measures the object signal features from the radar signal—i.e. the spatio-temporal pattern, such as object size, shape and movement characteristics. In addition, the first air quality monitor 300 uses RF scanning (WiFi or Bluetooth) to identify and record any characteristics of the devices that are broadcasting RF signals which are present when a person is present. After that, the first air quality monitor 300 runs some preliminary checks to see if the recognized features and radar-detected objects are relevant. The exact checks may vary, but the checks are intended to detect whether or not the radar signal actually corresponds to a living person. The weight given to each parameter, the parameters considered important, the applicable signal feature parameters for correction, and any other rules for performing the checks are set by the cloud server on a regular basis. After the checks are performed, the first air quality monitor 300 creates a unique personal signature for the person, including any mobile phone identification, and sends it to the server along with a timestamp. The server then checks to see if the unique personal signature matches any of the stored unique personal signatures; if it does, the server creates a record of the person being present in Room #1, and if it does not, the server stores the unique personal signature and creates an identifier for it, and then creates a record of the person being present in Room #1.

Figure 3C:
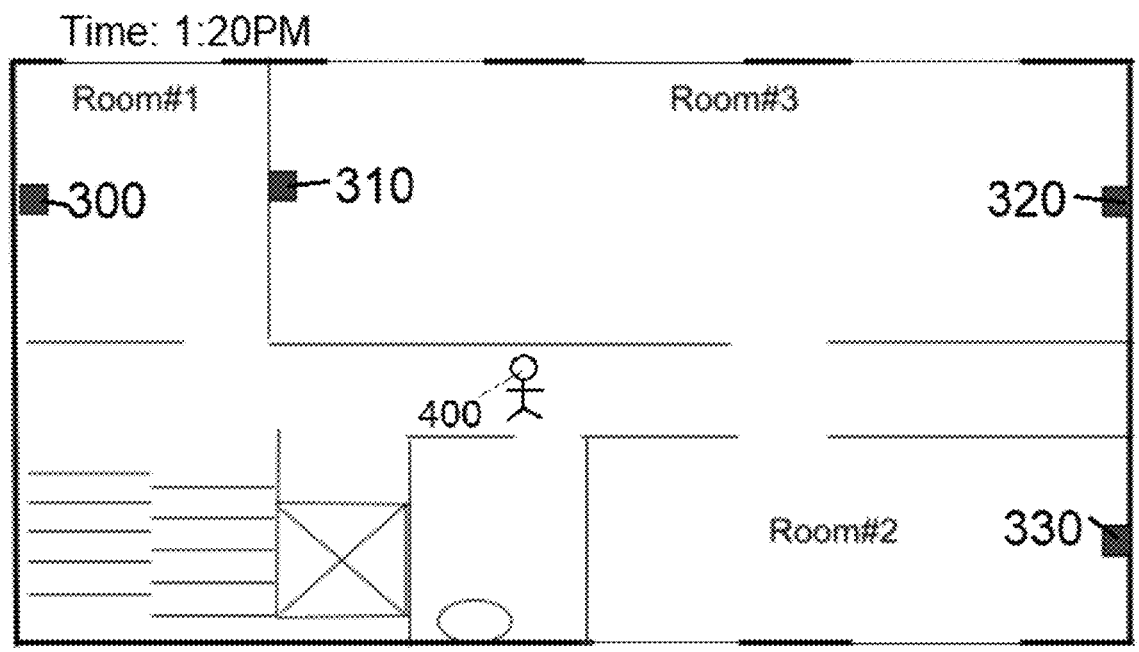
FIG. 3C shows a sample room diagram to illustrate the operation of the system of the present invention.

FIG. 3C shows what happens when the person leaves the room at 1:20 PM. The air quality monitor 300 sends this info (time stamps when the person entered and left the spaces, and the unique personal signature of the person) to the cloud. The cloud server then adds a record that the person left the room #1 at 1:20 pm.

Figure 3D:
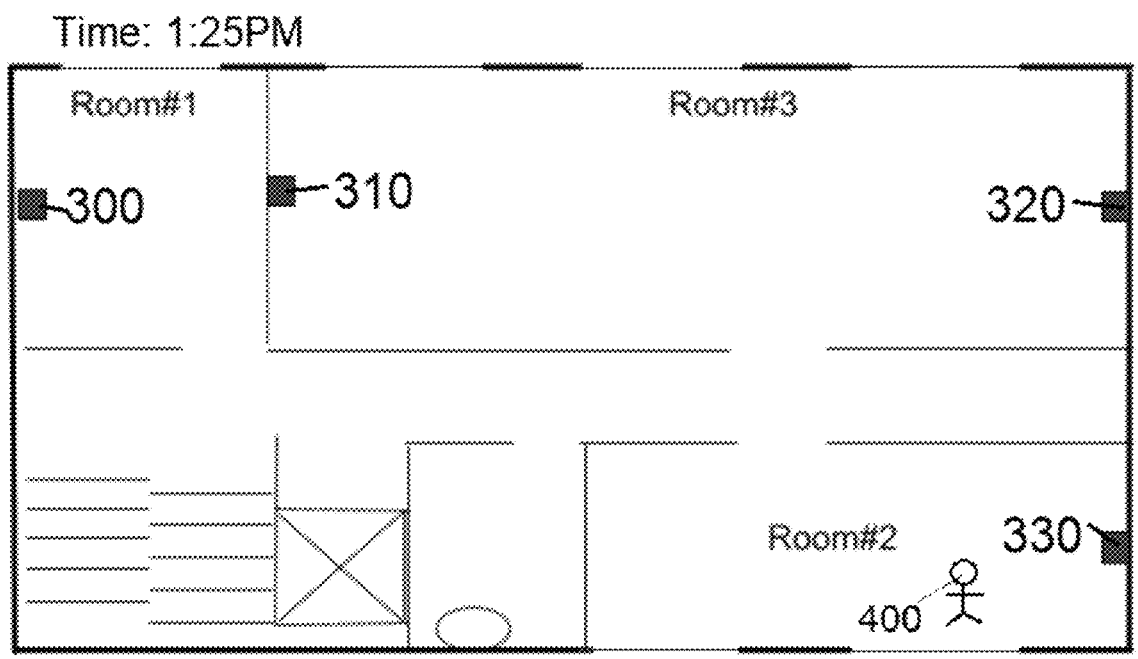
FIG. 3D shows a sample room diagram to illustrate the operation of the system of the present invention.

FIG. 3D shows the person entering room #2 at 1:25 PM. The same process is repeated for that room with regards to the air quality monitor 330, and the record of the time the person entered and exited the room will also be added to the server. The person's unique personal signature will be updated if necessary.

If the person 400 would go the room #3, and if 310 and 320 field of view overlap, then air quality monitor 310 and 320 may detect it. Then both 310 and 320 will send the timestamps when the person entered and exited the room and the person's unique personal signature. The server will combine these two records into one record after determining that they are of the same person.

It's important to state that both radar and RF scanning technologies has its limitations and cover different areas, so it's possible that not the whole room is covered and there are blind spots. And each air quality monitor can erroneously report that person left the room, even if the person is actually still there. Eventually it effects the accuracy of the personal pollution exposure, but overall gaps in timestamps can be measured. If the gaps are too high, the number of air quality monitors can be increased to cover more areas of the rooms.

After a predetermined amount of time, the server calculates the amount of time the person 400 spent in each room and combines that information with the air pollution data in each room to determine the person's cumulative pollution exposure.

It will be understood that the embodiments described herein are exemplary and not limiting, and that the invention is limited solely by the appended claims.

The invention claimed is:

1. A method for monitoring individual exposure to air pollution, comprising:
    using a plurality of air quality monitors to detect at least one air pollutant in a plurality of locations, wherein each air quality monitor comprises a RF scanner and a radar scanner;
    using at least one of the plurality of air quality monitors to perform the following actions:
        use the radar scanner to scan the vicinity of the air quality monitor;
        use the radar scanner to detect any living humans in the vicinity of the air quality monitor;
        use the radar scanner to determine the number of living humans present;
        record at least one radar parameter associated with each of the living humans detected, wherein the at least one radar parameter comprises at least one of the following: shape, size, movement patterns, location;
        use the RF scanner to detect any RF signals in the vicinity of the air quality monitor;
        use the RF signals to identify any mobile devices in the vicinity of the air quality monitor and a distance between each mobile device and the air quality monitor;
        analyze the at least one radar parameter associated with each of the living humans detected and the mobile devices identified by the RF scanner to determine which mobile devices are carried by which of the living humans;
        for each of the living humans where a mobile device is present, combine the at least one radar parameter and the mobile device identification to form a unique personal signature;
        for each of the living humans where a mobile device is not present, use the at least one radar parameter to form a unique personal signature;
        for each of the living humans where a radar parameter is not present, use the mobile device identification to form a unique personal signature;
        transmitting the unique personal signature to a server;
        transmitting a time stamp for the unique personal signature to the server;
    using the server to compare the unique personal signature with at least one stored unique personal signature;
    if the unique personal signature matches at least one stored unique personal signature, using the server to identify the person;
    if the unique personal signature does not match any of the at least one stored unique personal signature, storing the unique personal signature on the server and creating an identifier for a new person with the unique personal signature;
    using the server to determine entrance and exit timestamps using a first time and a second time for each person associated with a unique personal signature, wherein the first time is the time the person entered the vicinity of an air quality monitor and the second time is the time the person exited the vicinity of the air quality monitor;
    using the server to calculate each person's cumulative pollutant exposure based on air pollutant data received from each air quality monitor between the first time and the second time for the person.

2. The method of claim 1, further comprising:
    using the server to receive a first unique personal signature from a first air quality monitor;
    using the server to receive a second unique personal signature from a second air quality monitor, wherein the second air quality monitor is located in the same room as the first air quality monitor;
    using the server to identify the first unique personal signature and the second unique personal signature;
    using the server to compare the first unique personal signature and the second unique personal signature;
    using the server to identify if the first unique personal signature and the second unique personal signature correspond to the same person;
    if the first unique personal signature and the second unique personal signature are identified as the same person, performing one of the following actions:
        combining the first unique personal signature and the second unique personal signature into a new unique personal signature for the person;
        deleting the second unique personal signature.

3. The method of claim 1, further comprising:
    using the server to generate a log for each person, wherein the log comprises the times the person entered the vicinity of at least one air quality monitor and the times the person exited the vicinity of at least one air quality monitor, for a predetermined time interval.

4. The method of claim 1, wherein the step of combining the at least one radar parameter and the mobile device identification to form a unique personal signature further comprises:
    determining that at least one feature is irrelevant;
    eliminating the irrelevant feature from the unique personal signature.

5. The method of claim 1, wherein the step of using at least one of the plurality of air quality monitors to perform the following actions is performed at regular intervals.

6. The method of claim 1, wherein the step of using at least one of the plurality of air quality monitors to perform the following actions is triggered when motion is detected.

7. The method of claim 1, further comprising:
    if the server fails to identify whether the first unique personal signature and the second unique personal signature correspond to the same person, receiving input from a human regarding whether or not the first unique personal signature and the second unique personal signatures correspond to the same person.

* * * * *